(12) United States Patent
Martins et al.

(10) Patent No.: US 10,779,798 B2
(45) Date of Patent: Sep. 22, 2020

(54) ULTRASOUND THREE-DIMENSIONAL (3-D) SEGMENTATION

(71) Applicant: B-K Medical Aps, Herlev (DK)

(72) Inventors: Bo Martins, Rodovre (DK); Jens Munk Hansen, Copenhagen (DK)

(73) Assignee: B-K Medical ApS, Herlev (DK)

(*) Notice: Subject to any disclaimer, the term of this patent is extended or adjusted under 35 U.S.C. 154(b) by 51 days.

(21) Appl. No.: 16/139,279

(22) Filed: Sep. 24, 2018

(65) Prior Publication Data
US 2020/0093464 A1     Mar. 26, 2020

(51) Int. Cl.
G06T 7/50      (2017.01)
A61B 8/00     (2006.01)
A61B 8/08     (2006.01)
A61B 6/00     (2006.01)
G01S 7/52     (2006.01)

(52) U.S. Cl.
CPC ............ *A61B 8/466* (2013.01); *A61B 6/5223* (2013.01); *A61B 8/483* (2013.01); *G01S 7/52085* (2013.01); *G06T 7/50* (2017.01)

(58) Field of Classification Search
CPC ....... A61B 8/466; A61B 8/483; A61B 6/5223; G06T 7/50
See application file for complete search history.

(56) References Cited

U.S. PATENT DOCUMENTS

2008/0144903 A1* 6/2008 Wang ..................... G06T 15/08 382/130
2010/0179428 A1* 7/2010 Pedersen .................. A61B 8/00 600/443
2016/0217566 A1* 7/2016 Carmi ..................... G06T 5/002
2019/0083817 A1* 3/2019 Okusa ...................... A61B 8/08
2019/0167233 A1* 6/2019 Konofagou ............. A61B 8/08

OTHER PUBLICATIONS

Jing Yuan, Efficient 3D Endfiring TRUS Prostate Segmentation with Globally Optimized Rotational Symmetry, Published in: Computer Vision and Pattern Recognition (CVPR), 2013 IEEE Conference on, Published in: Med Image Computing Computer Assist Interv. 17(Pt 1): 796-803, 2014. PMID: 25333192, http://www.cv-foundation. org/openaccess/content_cvpr_2013/papers/Yuan_Efficient_3D_ Endfiring_2013_CVPR_paper.pdf.
Kaiming He, et al., Mask R-CNN, arXiv:1703.06870; https://arxiv. org/abs/1703.06870.
Splash of Color: Instance Segmentation with Mask R-CNN and TensorFlow. https://engineering.matterport.com/splash-of-color-instance-segmentation-with-mask-r-cnn-and-tensorflow-7c761e238b46.

* cited by examiner

*Primary Examiner* — Samantha (Yuehan) Wang
(74) *Attorney, Agent, or Firm* — Anthony M. Del Zoppo, III; Daugherty & Del Zoppo Co., LPA

(57) ABSTRACT

An ultrasound imaging system includes a beamformer configured to generate 2-D images offset from each other based on sweeping motion of a transducer array during a 3-D ultrasound imaging procedure producing volumetric data. The ultrasound imaging system further includes a 2-D mask processor configured to generate a 2-D mask image for each of the 2-D images. Each of the 2-D mask images includes a contour of a predetermined structure of interest in the volumetric data. The ultrasound imaging system further includes a 3-D mask processor configured to segment the structure from the 3-D image with the 2-D mask images, generating a 3-D segmentation.

20 Claims, 7 Drawing Sheets

ULTRASOUND THREE-DIMENSIONAL (3-D) SEGMENTATION

TECHNICAL FIELD

The following generally relates to ultrasound and more particularly to ultrasound three-dimensional (3-D) segmentation.

BACKGROUND

Medical ultrasound images are difficult to understand, e.g., because the ultrasound image is typically in an oblique view compared to the natural axis of an organ as well as the natural axis of the body. A consequence of the large variety of appearances of ultrasound images is that it can be difficult for humans and machines to learn to recognize, segment and label their content. Furthermore, it is often difficult to distinguish between fluid and attenuated tissue in an ultrasound image and this affects automatic gain control.

Another shortcoming is color flow imaging outside vessels where the data stems from tissue movement or mirroring in arterial vessel walls.

SUMMARY

Aspects of the application address the above matters, and others.

In one aspect, an ultrasound imaging system includes a beamformer configured to generate 2-D images offset from each other based on sweeping motion of a transducer array during a 3-D ultrasound imaging procedure producing volumetric data, a 2-D mask processor configured to generate a 2-D mask image for each of the 2-D images, wherein each of the 2-D mask images includes a contour of a predetermined structure of interest in the volumetric data, and a 3-D mask processor configured to segment the structure from the 3-D image with the 2-D mask images, generating a 3-D segmentation.

In another aspect, a method includes beamforming 2-D images offset from each other based on sweeping motion of a transducer array during a 3-D ultrasound imaging procedure producing volumetric data, generating a 2-D mask image for each of the 2-D images, wherein each of the 2-D mask images includes a contour of a predetermined structure of interest in the volumetric data, and segmenting the structure from the 3-D image with the 2-D mask images.

In yet another aspect, a computer-readable storage medium storing instructions that when executed by a computer cause the computer to perform a method for using a computer system to segment ultrasound imaging data, the method comprising: beamforming 2-D images offset from each other based on sweeping motion of a transducer array during a 3-D ultrasound imaging procedure producing volumetric data, generating a 2-D mask image for each of the 2-D images, wherein each of the 2-D mask images includes a contour of a predetermined structure of interest in the volumetric data, and segmenting the structure from the 3-D image with the 2-D mask images.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following generally describes a 3-D segmentation approach for ultrasound imaging. It also generally describes examples of utilizing the 3-D segmentation, e.g., to adjust image acquisition, visual presentation, etc.

Figure 1:
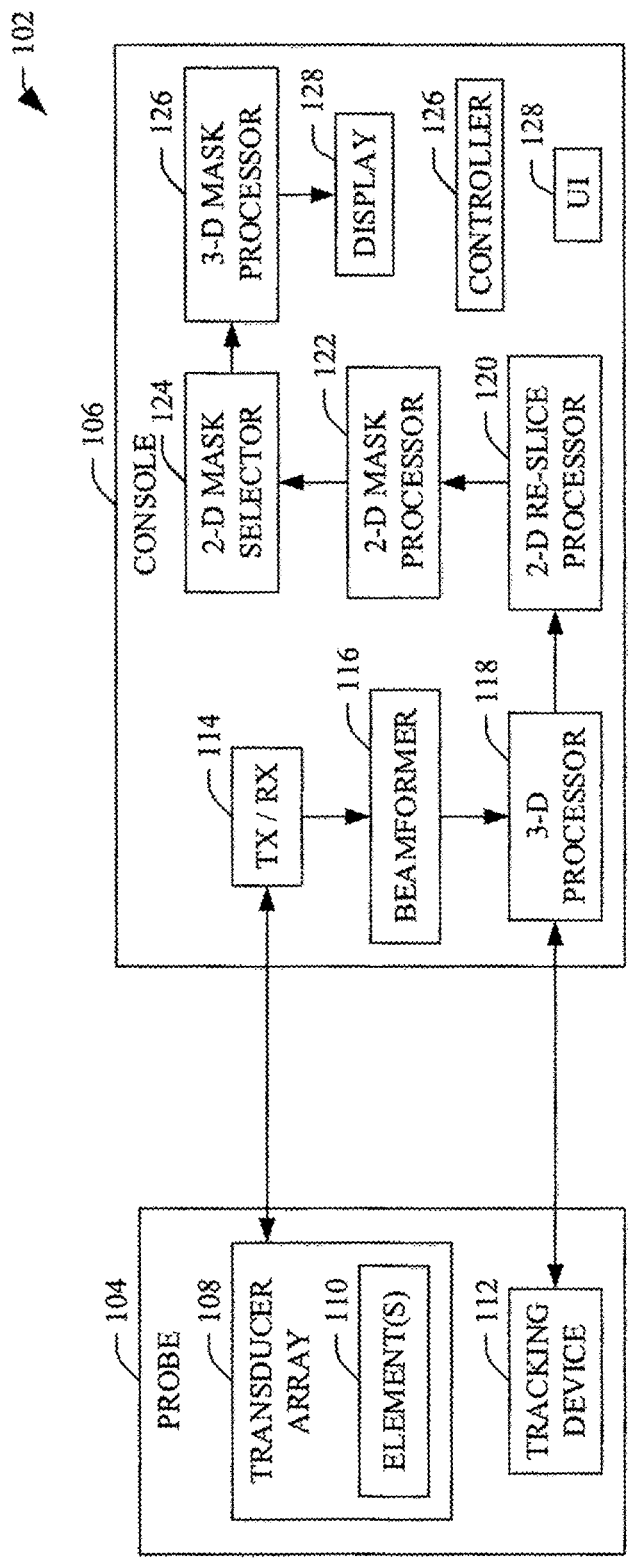
FIG. 1 schematically illustrates an example ultrasound system configured to perform a 3-D ultrasound image segmentation in accordance with an embodiment(s) described herein.

FIG. 1 illustrates an example ultrasound imaging system 102. The ultrasound imaging system 102 includes a probe 104 and an ultrasound console 106, which interface with each other through suitable complementary hardware (e.g., cable connectors and a cable, etc.) and/or wireless interfaces (not visible).

The probe 104 includes a transducer array 108 with one or more transducer elements 110. The transducer array 108 can be 1-D or 2-D, linear, curved, and/or otherwise shaped, fully populated, sparse and/or a combination thereof, etc. array. A suitable probe includes an endocavitary and/or other probe.

Figure 2:
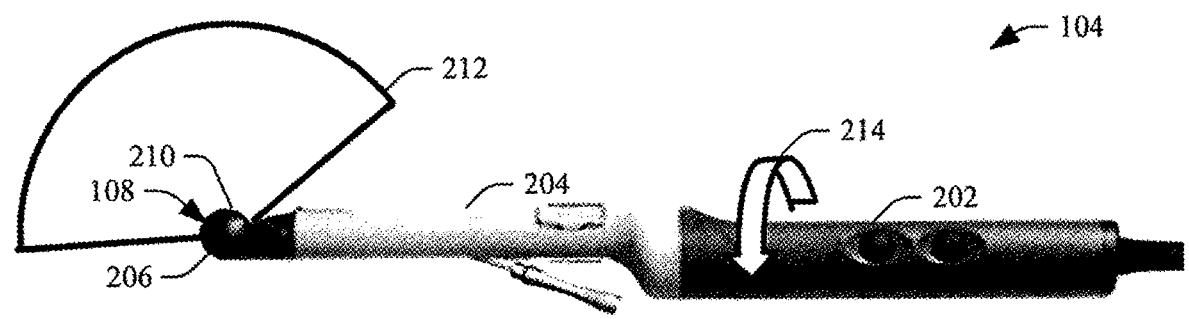
FIG. 2 illustrates an example ultrasound probe of the system of FIG. 1 in accordance with an embodiment(s) described herein.

In one instance, a user rotates the transducer array 108 to acquire a series of 2-D images that are then combined to produce 3-D volumetric data. FIG. 2 illustrates an example of such a probe, which includes a handle 202, a shaft 204, a head 206, the array 108 behind an acoustic window 210 and configured to provide a sagittal field of view (FOV) 212. Example rotation is shown at 214. The probe 104 of course can be rotated in the opposite direction and/or translated. Another example probe is described in U.S. Pat. No. 9,259, 208 B1, filed Oct. 20, 2009, and entitled "Ultrasound Probe," which is incorporated herein by reference in its entirety. Other probes are also contemplated.

In another instance, the transducer array 108 is configured to mechanically and/or electrically rotate within the probe 104 to acquire such 2-D images. Non-limiting examples of such a probe is described in U.S. Pat. No. 9,289,187 B2, titled "Imaging Transducer Probe," and filed Jun. 10, 2013, which is incorporated herein by reference in its entirety, and US 2018/0185008 A1, titled "US Imaging Probe with an US Transducer Array and an Optical Imaging Subsystem," and filed Dec. 19, 2017, which is incorporated herein by reference in its entirety. Other probes are also contemplated herein.

Returning to FIG. 1, the one or more transducer elements 110 are configured to convert an excitation electrical signal to an ultrasound pressure field. The one or more transducer elements 110 are also configured to convert a received ultrasound pressure field (an echo) into an electrical (e.g., analog radio frequency, RF) signal. The received ultrasound pressure field, in one instance, is produced in response to a transmitted ultrasound pressure field interacting with structure, e.g., a prostate a bladder, a vessel, and/or other tissue.

The probe 104 further includes a probe tracking device 112. In one instance, the probe tracking device 112 is internal to the probe 104. In another instance, the probe tracking device 112 is external to the probe 104. In yet another instance, the probe tracking device 112 is partially internal and partially external to the probe 104. Examples of suitable probe tracking devices include, but are not limited to inertial, absolute, motorized, optical, magnetic, etc.

An example inertial tracking device includes an accelerometer, a gyroscope and/or a magnetometer and generate signals indicative of an orientation and/or a velocity. An example optical tracking device includes elements affixed to a handle of the probe 104 and tracked via an optical video camera. An example magnetic tracking device includes coils on the probe 104 and calculates position and orientation by a relative magnetic flux of the coils. Non-limiting example of suitable tracking devices are discussed in Birkfellner et al., "Tracking Devices," In: Peters T., Cleary K. (eds) Image-Guided Interventions. Springer, Boston, Mass., 2008.

The console 106 includes transmit and receive circuitry (TX/RX) 114 configured to generate the excitation signal conveyed to the transducer array 108 for at least 3-D imaging by manual and/or electrical-mechanical sweeping of the transducer array 108. The TX/RX 114 is also configured to process the electrical signal corresponding to the received echo signal. The TX/RX 114, in one instance, is further configured to pre-condition and/or pre-process the signal (e.g., amplify, digitize, etc.). Other processing is also contemplated herein.

The illustrated embodiment shows the transmit and receive operations are performed by the same circuitry, the TX/RX 114. In a variation, the transmit and receive operations are performed by separate circuitry, e.g., transmit circuitry for transmit operations and separate receive circuitry for receive operations. One or more switches and/or other device(s) can be used to switch between transmit and receive operations and/or transmit and receive circuitry by electrically connecting and electrically disconnecting transmit and receive circuitry.

The console 106 further includes a beamformer 116. In one instance, the beamformer 116 is configured to beamform the signal, e.g., via delay-and-sum beamforming and/or other beamforming. For B-mode imaging, this includes generating a sequence of focused, coherent echo samples along focused scanlines of a scanplane to produce a 2-D image. When the probe 104 is rotated during image acquisition, the beamformer 116 generates a series of angularly spaced 2-D images. The relative position of each image with respect to each other is indicated by the signal from the tracking device 112.

The console 106 further includes a 3-D processor 118. The 3-D processor 118 is configured to generate a 3-D image from the series of 2-D images generated while rotating the probe 104 during imaging based on the signal from the tracking device 112. In one instance, the 3-D processor 118 generates the 3-D image by interpolating between neighboring 2-D images.

The console 106 further includes a 2-D re-slice processor 120. In one instance, the 2-D re-slice processor 120 is configured to re-slice the 3-D image into a predetermined number of 2-D slices/images. For example, in one instance the 2-D re-slice processor 120 generates thirty (30) 2-D slices, each spaced six (6) degrees away from its neighboring 2-D slice(s). In another instance, the 2-D re-slice processor 120 generates sixty (60) 2-D slices, each spaced three (3) degrees away from its neighboring 2-D slice(s). Other numbers of slices and angular increments (e.g., from 1-10) are also contemplated herein. The number and/or angular increment may depend on the particular object being scanned, the complexity of the object, processing time constraints, etc. Offsets other than angular are also contemplated herein. An example is the translatory motion along one side of the neck of an ultrasound transducer placed transversely on the neck to insonify a lobe of the thyroid. Another example is the translatory motion along the body axis of an ultrasound transducer being perpendicular to the axis of motion insonifying the aorta.

In general, the user will center the transducer array at a middle of the object during scanning. The 2-D re-slice processor 120 re-slices the 3-D image with an anatomical axis of interest. e.g., a rotational symmetry automatically based on the location of the centered transducer array with respect to the object during scanning, an anatomical axis of interest automatically based on another body part and/or an anatomical axis of interest automatically based on the body. This is in stark contrast to a system which requires a user to select a best possible axis in an attempt to optimize for symmetry. As such, the approach described herein does not require user interaction and/or input to identify the axis and is thus entirely automated. This may also reduce the demand for objects for training the algorithm and/or increase accuracy. In another embodiment, the 2-D re-slice processor 120 utilizes a user selected axis.

Figure 3:
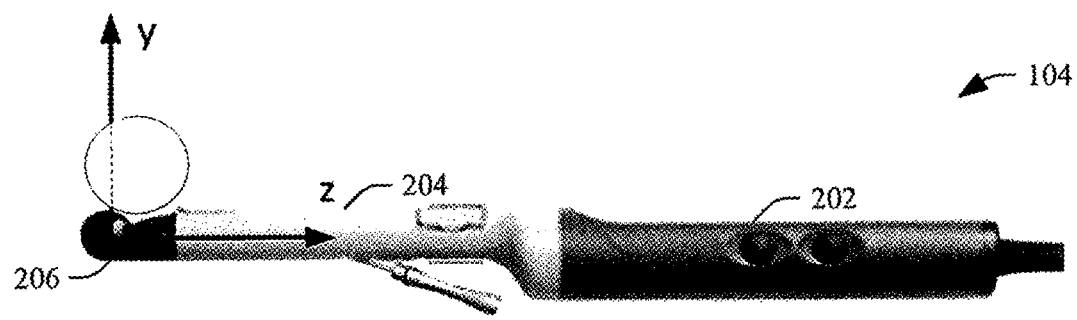
FIG. 3 illustrates an example frame of reference for the ultrasound probe of FIG. 2 in accordance with an embodiment(s) described herein.
Figure 4:
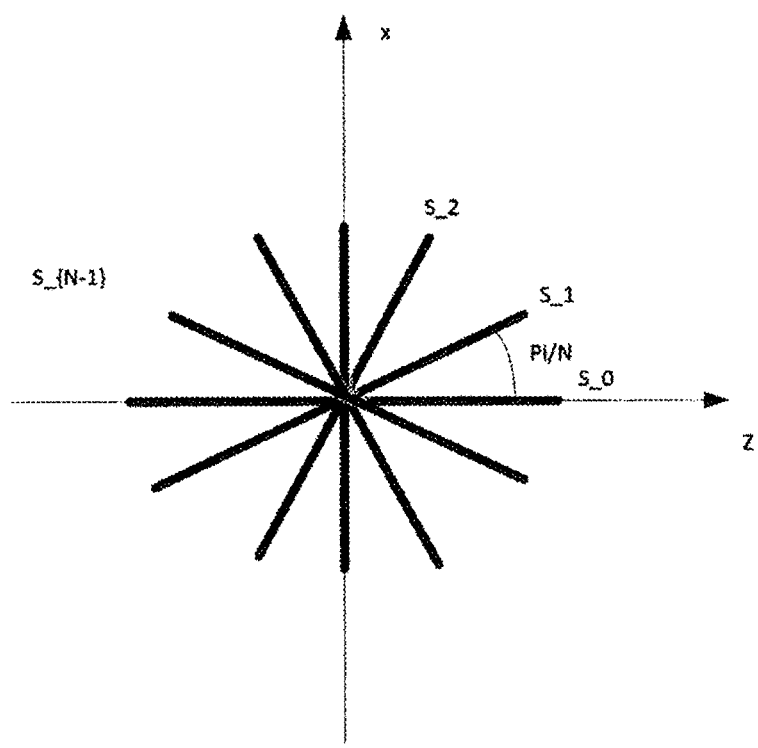
FIG. 4 illustrates an example approach for re-slicing a 3-D image into equiangular 2-D images in accordance with an embodiment(s) described herein.
Figure 5:
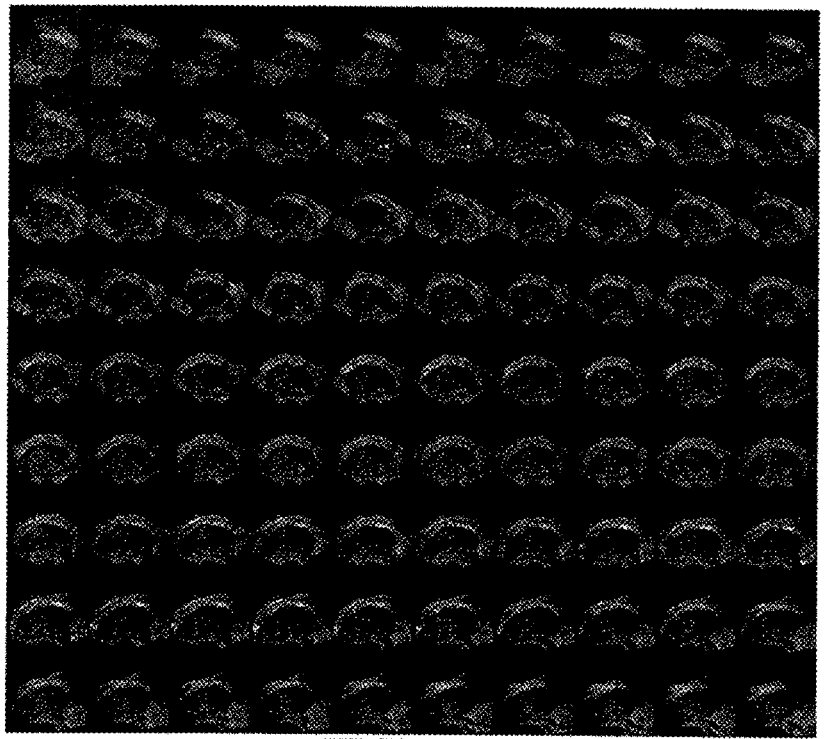
FIG. 5 illustrates an example of a plurality of re-sliced 2-D images in accordance with an embodiment(s) described herein.

FIG. 3 show a frame of reference/coordinate system with the origin at the geometrical center of the sagittal array. The user will typically have the tissue of interest in the center of the sweep. The x-axis points into the figure. The y-axis is defined as the line in the xy-plane that splits the total sweep angle in two equal parts. The z-axis points in the direction of the shaft 204 of the probe 104. The z-axis is normal to the xy-plane. The yz-plane is the sagittal body plane. The coordinate (x,y,z) forms a right-hand coordinate system. In FIG. 4, the 2-D re-slice processor 120 re-slices the 3-D image so that all N slices contain the y-axis and are perpendicular to the xz-plane and are spaced with equal angular distance making the angle between the slices it/N. FIG. 5 shows an example with ninety (90) re-sliced 2-D images of a prostate.

Returning to FIG. 1, the console 106 further includes a 2-D mask processor 122. The 2-D mask processor 122 is configured to generate at least a 2-D mask for each re-sliced 2-D image. In one instance, the 2-D mask processor 122 utilizes a convolutional neural network for predicting objects masks and bounding boxes to generate the 2-D masks. One instance of such a network is a modified Mask Region-Convolutional Neural Network (Mask R-CNN), where the modification includes outputting a mask in a floating-point mathematical representation (e.g., float32 with values between $1e^{-9}$ (0.000000001) and 1.000000000) instead of a binary (0 or 1) representation. In one instance, this allows for limiting quantization error during the reconstruction of a 3-D mask from a set of 2-D masks relative to systems, which utilize a binary mathematical representation.

Figure 6:
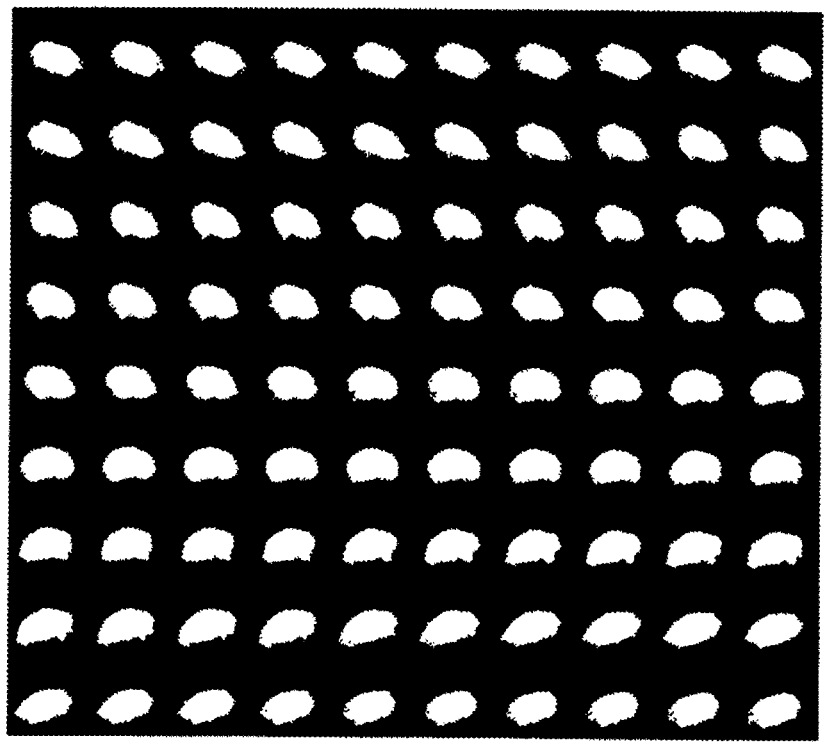
FIG. 6 illustrates an example of a plurality 2-D image masks corresponding to the re-sliced 2-D images of FIG. 5 in accordance with an embodiment(s) described herein.

The Mask R-CNN algorithm is further discussed in detail in "MaskR-CNN," He et al., 24 Jan. 2018. As discussed therein, the Mask R-CNN algorithm uses a two-stage procedure. In the second stage, the Mask R-CNN algorithm classifies individual objects in an image and localizes each with a labeled bounding box, in parallel with generating a binary mask for each object in a bounding box. The mask branch is a Fully Convolutional Network (FCN) applied to each region of interest, predicting a segmentation mask in a pixel-to-pixel manner. The Mask R-CNN algorithm also outputs a confidence metric or level (e.g., as a percentage) for each mask that indicates a confidence that the object classification is correct. FIG. 6 shows masks corresponding to the re-sliced 2-D images of FIG. 5. In everything that follows, the modified Mask R-CNN algorithm will be used for generating 2-D masks, but the 2-D mask processor could be replaced by another neural network-based algorithm, which generates 2-D mask using prior information obtained through training.

Returning to FIG. 1, the console 106 further includes a 2-D mask selection processor 124. The 2-D mask selection processor 124 is configured to select all or less than all (i.e. a subset) of the re-sliced 2-D images to reconstruct. For this, the 2-D mask selection processor 124 utilizes the confidence level computed and output by the Mask R-CNN algorithm for each 2-D mask image. The confidence level, e.g., is a value from zero to one (0-1) and indicates a confidence that an outline/perimeter of tissue of interest in a mask is the true perimeter, wherein a higher value indicates a greater confidence.

In one instance, the 2-D mask selection processor 124 compares the confidence level generated by the Mask R-CNN algorithm with a predetermined threshold (e.g., 70%). The 2-D mask selection processor 124 selects 2-D masks with confidence levels that satisfy the predetermined threshold as images to reconstruct. The threshold can be a default, a user preference, adjustable, static, etc. Calcifications can cast shadows making it difficult or impossible to recognize the prostate outline with high confidence in some 2-D masks. These 2-D masks are excluded from the reconstruction of the 3-D mask. This may improve the accuracy of the reconstruction relative to a system that just uses all of the 2-D masks.

Before using the Mask R-CNN algorithm, the Mask R-CNN algorithm is trained with "ground truth" data and training data. The "ground truth" data, e.g., is a 3-D segmentation of tissue of interest. In one interest, the 3-D segmentation is produced through a semi-automated process that includes expert (e.g., clinician) involvement (e.g., free hand segmentation) and confirmation. In another instance, the 3-D segmentation is produced through a computer fully automated process with expert confirmation. The training data includes images re-sliced from the "ground truth" 3-D data.

The console 106 further includes a 3-D mask processor 126. The 3-D mask processor 126 is configured to reconstruct a 3-D mask/segmentation of the tissue of interest only with the 2-D masks with confidence levels that satisfied the predetermined threshold. In one instance, the 3-D mask processor 126 reconstructs the 3-D mask by interpolating between neighboring 2-D masks. The 3-D mask processor 126 computes a volume measurement of the tissue based on the 3-D mask, which is a numerical quantity of a 3-D space enclosed by an external surface of the 3-D mask/segmentation. In another instance, the volume measurement is computed without generating a 3-D mask, e.g., by adding r*\delta \theta, for each pixel in the 2-D masks of all the slices, where r denotes the distance from a mask pixel to the approximate axis of rotation and \delta \theta denotes the angle between the previous and the next good image plane for the image to which the current mask pixel belongs.

Figure 7:
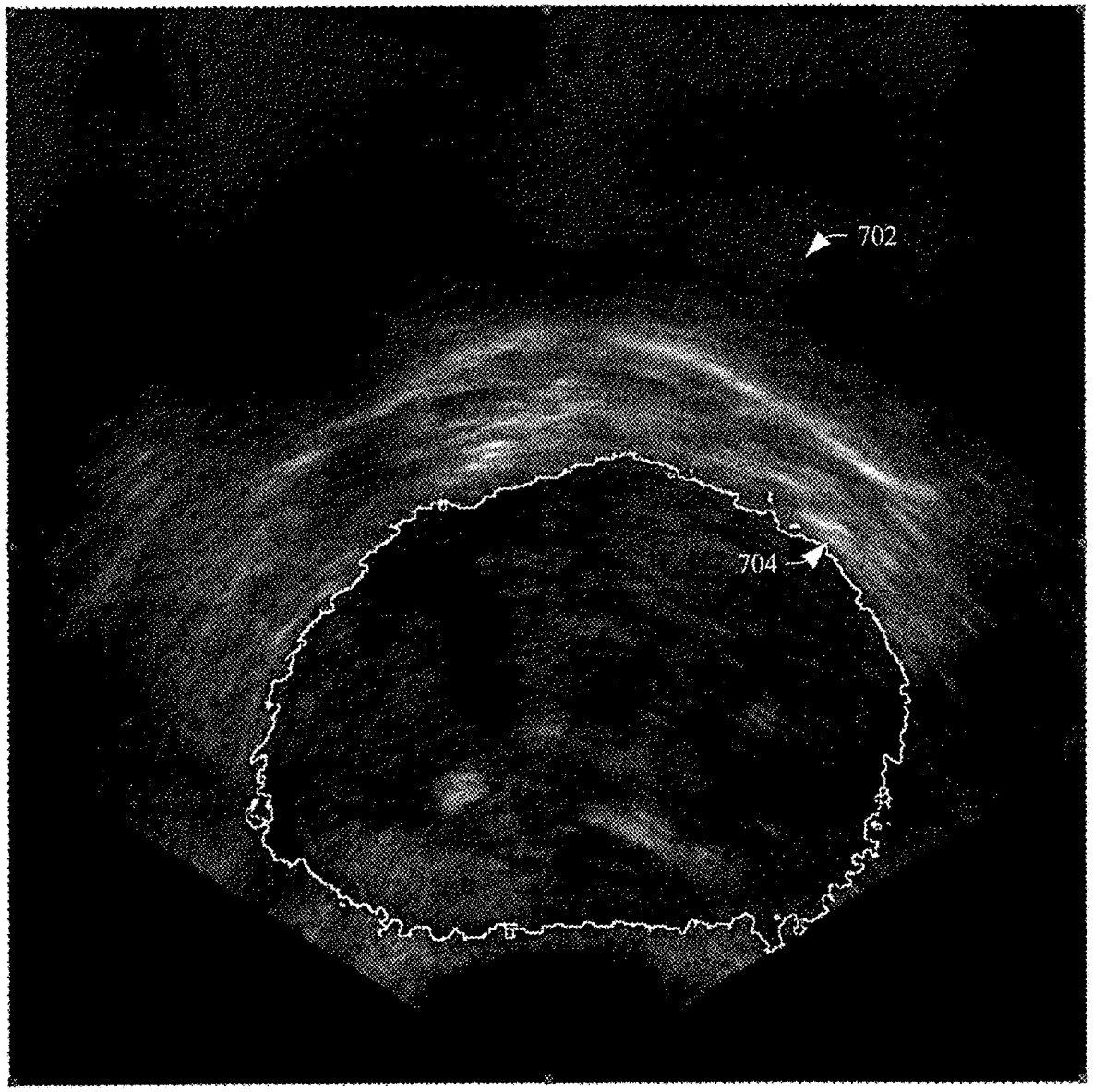
FIG. 7 illustrates an example 2-D image with a corresponding 2-D mask image overlaid thereover in accordance with an embodiment(s) described herein.

The console 106 further includes a display 128. In one instance, an image of the reconstructed volume is displayed via the display 128 with the corresponding 2-D mask image overlaid over the 2-D image. This may allow the user to quickly verify that the segmentation is correct. FIG. 7 shows an example of an image 702 including a prostate with a 2-D mask image 704 overlaid over the prostate in the image 702. Besides the volume measurement, a height, width and length can be computed by the system for the object that is outlined by the 3-D mask and be displayed. Alternatively, or additionally, user-adjustable height, width and length caliper computer tools are placed in sagittal and transverse views allowing the user to calculate the prostate volume in a more traditional way.

It is to be appreciated that one or more of the beamformer 116, the 3-D processor, the 2-D re-slice processor 120, the 2-D mask processor 122, the 2-D mask selector 124 and/or the 3-D mask processor 126 is implemented via a computer processor (e.g., central processing unit (CPU), microprocessor, etc.). For example, in one instance, one or more of the beamformer 116, the 3-D processor, the 2-D re-slice processor 120, the 2-D mask processor 122, the 2-D mask selector 124 and/or the 3-D mask processor 126 are implemented by way of processor executing computer readable instructions, encoded or embedded on computer readable storage medium (which excludes transitory medium).

The automated 3-D segmentation approach described herein mitigates having a user define the axis of rotation, which reduces overall processing time relative to a system in which the user defines the axis of rotation and thus is an improvement to an existing technological process. However, the automated 3-D segmentation approach described herein is not just an automation of an existing non-computerized process in a same manner. Furthermore, 2-D mask images that do not produce a highly confident contours are not used to segment the structure in 3-D or compute the volume measurement, mitigating error introduced from calcifications, etc. obscuring visibility in parts of the structure of interest and thus improves accuracy. Furthermore, the approach described herein allows a user to determine an acceptable fidelity of the segmentation.

In a variation, the 2-D re-slice processor 120 is omitted or bypassed and the 2-D mask processor 122 generates the 2-D masks with the beamformed 2-D images.

The approach described herein is well-suited for segmenting 3-D tissue such as a prostate, a bladder, a vessel, etc. The 3-D segmentation can be used to adjust visual presentation, image acquisition and/or other parameters. The following provides some non-liming examples.

In general, automatic time gain control (TGC) algorithms try to compensate for the difference between the average soft tissue attenuation of 0.5 dB/(cm MHz) and the actual attenuation, which may be much lower due to fluids attenuate the signals much less. Other phenomena which affect the image brightness include uneven transducer contact, rib shadows, and reflecting interfaces. In order to deliver a uniform image to the user, the above is taken into account and the 3-D segmentation approach described herein provides information for adjusting the gain properly.

Figure 8:
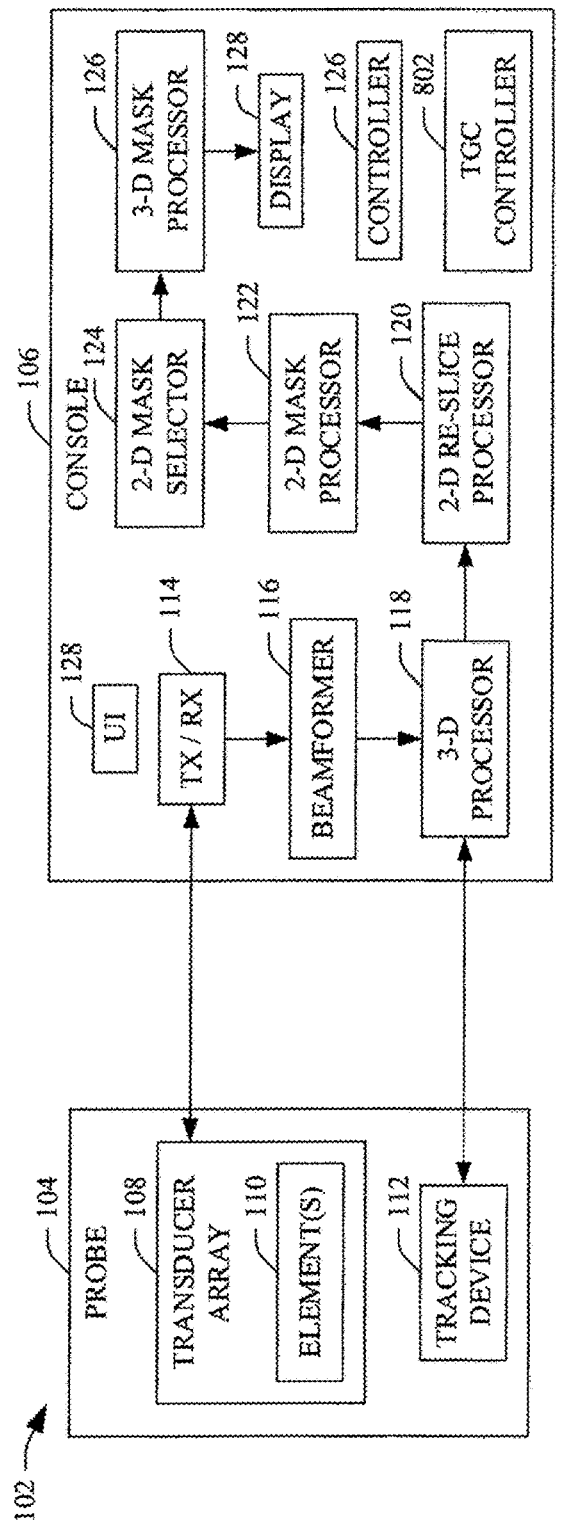
FIG. 8 schematically illustrates a variation of the embodiment of FIG. 1 in accordance with an embodiment(s) described herein.

For example, the approach described herein improves the ability to distinguish between fluid and attenuated tissue in an ultrasound image for TGC. In one instance, a TGC controller 802 (FIG. 8) employs the confidence level to reduce the weight of sample values inside likely fluid collections, regardless of whether these collections also have weak tissue signals. By doing so, temporal effects of fluctuating image brightness based on whether or not a particular area of the image were identified as being a fluid collection or not are mitigated. This mitigates instances where it is difficult to distinguish between fluid and attenuated tissue in an ultrasound image.

A non-limiting example of a suitable time gain compensation is described in international application publication number WO2017/122042A1, titled "Automatic Time Gain Compensation (TGC) in Ultrasound Imaging," and filed Jul. 10, 2018, which is incorporated herein by reference in its entirety. In the approach described in WO2017/122042A1, the confidence level can be used in conjunction with the TGC matrices to reduce the weight of sample values inside likely fluid collections, regardless of whether these collections also have weak tissue signals. The confidence level can also be employed with other TGC approaches.

Figure 9:
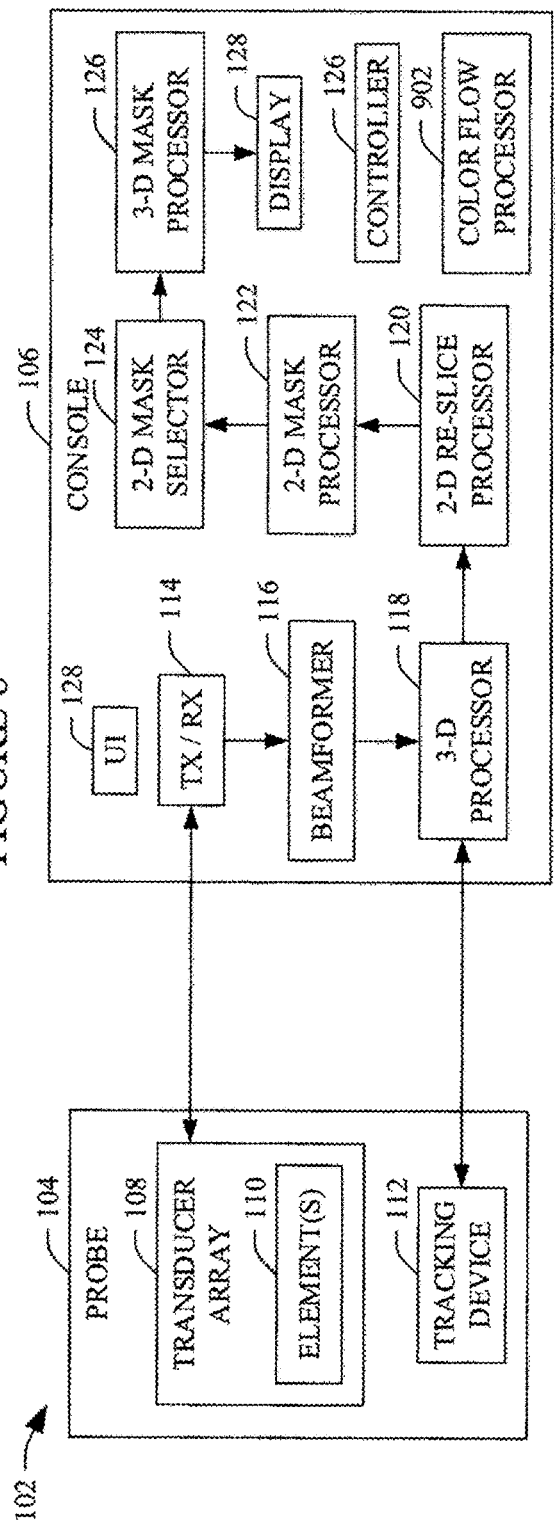
FIG. 9 schematically illustrates another variation of the embodiment of FIG. 1 in accordance with an embodiment(s) described herein.

In another example, the approach described herein is used to make a vessel mask for removal of color flow outside vessels, where the false color flow may stem from tissue movement or may be a result of mirroring in the vessel wall itself such as the carotid artery. With the 3-D segmentation described herein, organs are delineated properly, and it is possible to erase unwanted color flow. For instance, a color flow processor 902 (FIG. 9) employs the vessel mask to suppress color signals outside of this mask, which mitigates the problem is color flow imaging outside vessels where the data stems from tissue movement or mirroring in arterial vessel walls.

Figure 10:
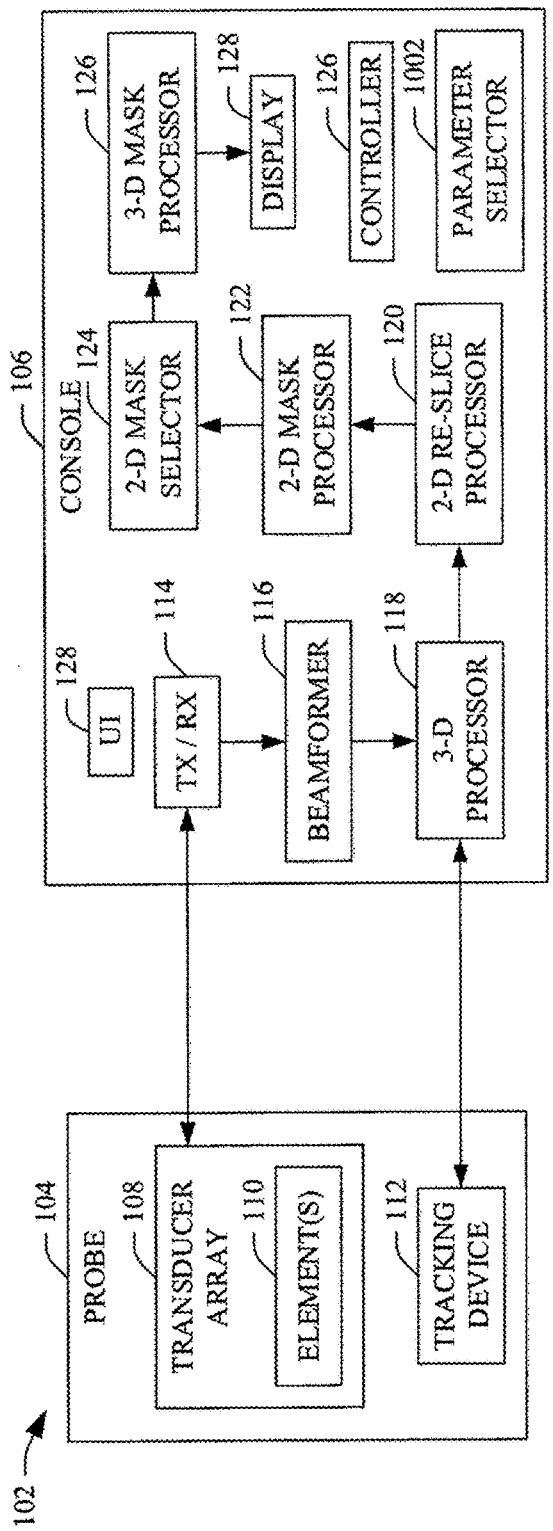
FIG. 10 schematically illustrates yet another variation of the embodiment of FIG. 1 in accordance with an embodiment(s) described herein.
Figure 11:
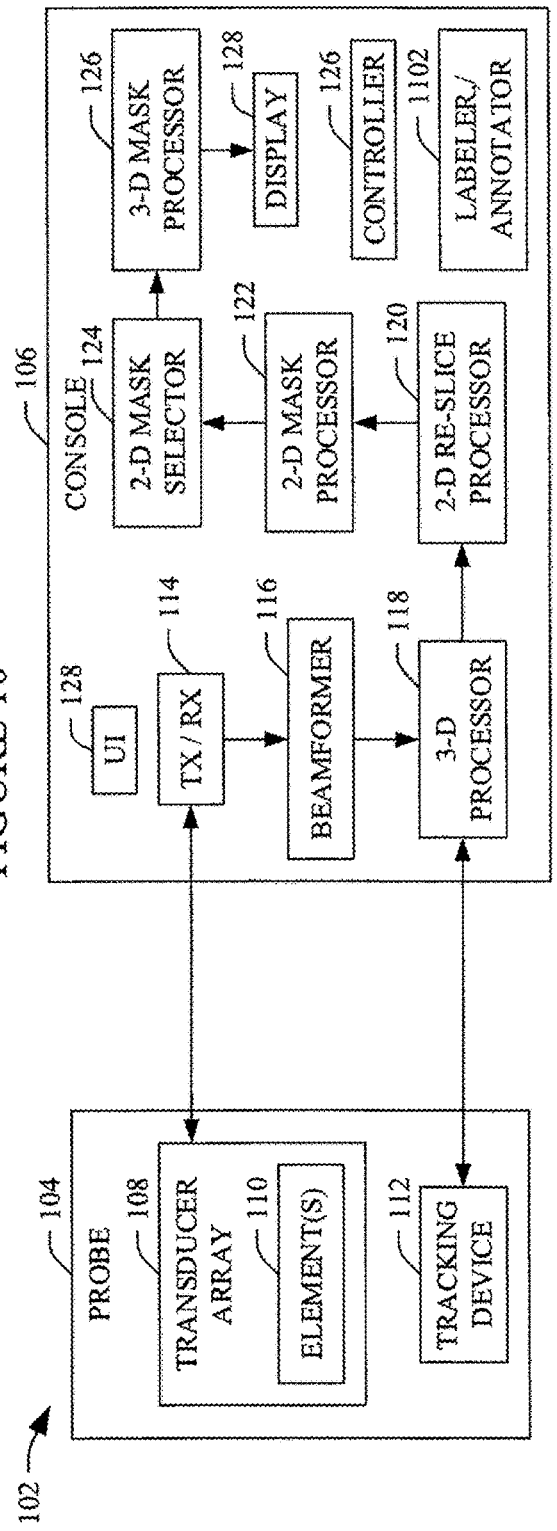
FIG. 11 schematically illustrates still another variation of the embodiment of FIG. 1 in accordance with an embodiment(s) described herein.

In another example, the approach described herein allows for modifying image acquisition. For example, where an image includes both the liver and a kidney, which are identified by the detection algorithm, the user can select an organ of interest (the liver or the kidney) by actuating a control that invokes a parameter selector 1002 (FIG. 10) to automatically select parameters such as depth, frequency, color box position, pulse repetition frequency, color parameters, etc. Furthermore, a labeler/annotator selector 1102 (FIG. 11) labels and/or annotates tissue to spatially identify tissue, such as the kidneys, which include a pair (e.g., left and right) of structures.

In another example, the approach described herein can be used to assist surgery. For example, a 3-D ultrasound volume of part of the brain can be created during surgery to assist locating brain structures that were shifted once the skull was opened. Segmentation of a potential tumor as well as identification and segmentation of important structures that need to be preserved will be important to the success of the surgery.

In another embodiment, two or more of the embodiments described in FIGS. 8, 9, 10 and 11 are combined together.

Figure 12:
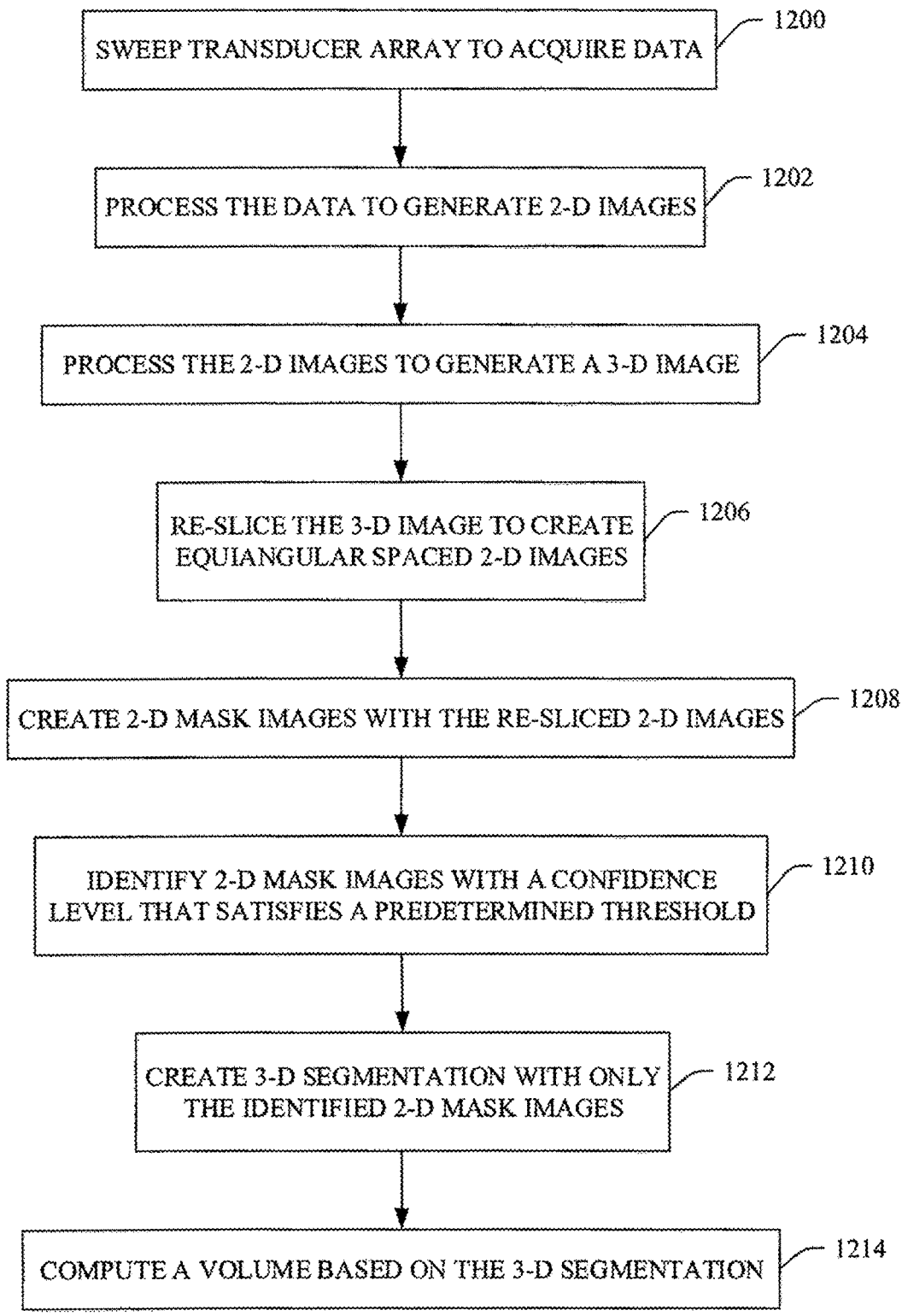
FIG. 12 illustrates an example method in accordance with an embodiment(s) described herein.

FIG. 12 illustrates an example method in accordance with an embodiment herein.

At 1200, the transducer elements 110 are swept over tissue of interest to acquire data.

In one instance, this includes first locating the tissue of interest such that the entire tissue of interest is displayed. This may entail centering the transducer array 108 on the central axis of the tissue of interest. Then, the probe 104 is rotated in one direction until the tissue of interest is no longer in the field of view. Then the probe 104 is rotated in the opposite direction while scanning until again the tissue of interest is no longer in the field of view to capture data for the entire volume.

At 1202, the acquired data are processed to generate a series of 2-D images angularly offset from each other based on the sweep rotation, as described herein and/or otherwise.

At 1204, the series of 2-D images are processed to generate a 3-D image, as described herein and/or otherwise.

At 1206, the 3-D image is processed to create a predetermined number of re-sliced 2-D images separated by a same predetermined angular width, as described herein and/or otherwise.

At 1208, 2-D mask images are generated with the re-sliced 2-D images.

At 1210, 2-D mask images with a predetermined contour confidence are identified, as described herein and/or otherwise.

At 1212, the identified 2-D mask images are processed to segment tissue of interest in 3-D, as described herein and/or otherwise.

At 1214, a volume of the tissue of interest is computed based on the 3-D segmentation, as described herein and/or otherwise.

Optionally, a 2-D image is displayed with a corresponding 2-D mask image overlaid thereover.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium, which is not computer readable storage medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a beamformer configured to generate a series of 2-D images that are angularly offset from each other based on a sweep angle of a rotating transducer array during a 3-D ultrasound imaging procedure producing volumetric data;
   a 3-D image processor configured to construct a 3-D image from the series of 2-D images;
   a 2-D re-slice processor configured to generate a set of re-sliced angularly offset 2-D images from the 3-D image based on a predetermined angular distance between the re-sliced 2-D images, wherein at least one of the re-sliced 2-D images has a major plane that is not parallel to major planes of the 2-D images in the series of 2-D images;
   a 2-D mask processor configured to generate a 2-D mask image for a plurality of the re-sliced 2-D images, wherein each of the 2-D mask images includes a contour of a predetermined structure of interest in the volumetric data; and a 3-D mask processor configured to segment the structure of interest from the 3-D image based on the 2-D mask images, generating a 3-D segmentation.

2. The ultrasound imaging system of claim 1, further comprising:
a display configured to display a re-sliced 2-D image with a corresponding 2-D mask overlaid thereover.

3. The ultrasound imaging system of claim 1, where the 3-D mask processor is further configured to compute a volume measurement of the structure from the 3-D segmentation.

4. The ultrasound imaging system of claim 1, wherein the series of 2-D images extend along a z-axis of the transducer array and are angularly offset from each other in an x-y plane of a Cartesian coordinate system, and the re-sliced images are angularly offset from each other in an x-z plane of the Cartesian coordinate system.

5. The ultrasound imaging system of claim 4, wherein the 2-D mask processor is configured to further generate a confidence level for each of the 2-D mask images, and further comprising:
a 2-D mask selector configured to identify a set of the 2-D mask images with confidence levels that satisfy a predetermined confidence threshold, wherein the 3-D mask processor is configured to segment the structure from the 3-D image only with the identified 2-D mask images.

6. The ultrasound imaging system of claim 5, wherein the set includes less than all of the 2-D mask images.

7. The ultrasound imaging system of claim 1, further comprising:
a time gain control controller configured to control a gain of pixels of the 2-D images based on the 3-D segmentation.

8. The ultrasound imaging system of claim 1, further comprising:
a color flow processor configured to remove color flow outside of a vessel based on the 3-D segmentation.

9. The ultrasound imaging system of claim 1, further comprising:
a parameter selector configured to automatically select acquisition or visualization parameters based on a user input selecting tissue of interest where the 2-D mask processor identifies more than one type of tissue in the 2-D images.

10. The ultrasound imaging system of claim 1, further comprising:
a labeler configured to label or annotate tissue to spatially identify tissue that includes a pair of or many structures.

11. A method, comprising:
beamforming a series of 2-D images that are angularly offset from each other based on a sweep angle of a rotating transducer array during a 3-D ultrasound imaging procedure producing volumetric data;
generating a 3-D image from the series of 2-D images;
generating a set of re-sliced angularly offset 2-D images from the 3-D image based on a predetermined angular distance between the re-sliced 2-D images, wherein at least one of the re-sliced 2-D images has a major plane that is not parallel to major planes of the 2-D images in the series of 2-D images;
generating a 2-D mask image for a plurality of the re-sliced 2-D images, wherein each of the 2-D mask images includes a contour of a predetermined structure of interest in the volumetric data; and
segmenting the structure of interest from the 3-D image with the 2-D mask images.

12. The method of claim 11, further comprising:
computing a numerical quantity of a 3-D space enclosed by an external surface of the segmented structure.

13. The method of claim 12, wherein the series of 2-D images extend along a z-axis of the transducer array and are angularly offset from each other in an x-y plane of a Cartesian coordinate system, and the re-sliced images are angularly offset from each other in an x-z plane of the Cartesian coordinate system.

14. The method of claim 13, further comprising:
generating a confidence level for each of the 2-D mask images; and
identifying a set of the 2-D mask images with confidence levels that satisfy a predetermined confidence threshold, wherein the structure is segmented from the 3-D image only with the identified 2-D mask images.

15. The method of claim 14, further comprising:
displaying a re-sliced 2-D image with a corresponding 2-D mask overlaid thereover.

16. A computer-readable storage medium storing instructions that when executed by a computer cause the computer to perform a method for using a computer system to segment ultrasound imaging data, the method comprising:
beamform a series of 2-D images that are angularly offset from each other based on a sweep angle of a rotating transducer array during a 3-D ultrasound imaging procedure producing volumetric data;
generating a 3-D image from the series of 2-D images;
generating a set of re-sliced angularly offset 2-D images from the 3-D image based on a predetermined angular distance between the re-sliced 2-D images, wherein at least one of the re-sliced 2-D images has a major plane that is not parallel to major planes of the 2-D images in the series of 2-D images;
generating a 2-D mask image a plurality of the 2-D images, wherein each of the 2-D mask images includes a contour of a predetermined structure of interest in the volumetric data; and
segmenting the structure of interest from the 3-D image with the 2-D mask images.

17. The computer-readable storage medium of claim 16, the method further comprising:
computing a volume of the structure from the segmented structure by adding r*\delta \theta, for each pixel in the 2-D mask images, where r denotes a distance from a mask pixel to an approximate axis of rotation and \delta \theta denotes an angle between a previous and a next good image plane for an image to which a current mask pixel belongs.

18. The computer-readable storage medium of claim 17, wherein the series of 2-D images extend along a z-axis of the transducer array and are angularly offset from each other in an x-y plane of a Cartesian coordinate system, and the re-sliced images are angularly offset from each other in an x-z plane of the Cartesian coordinate system.

19. The computer-readable storage medium of claim 18, the method further:
generating a confidence level for each of the 2-D mask images; and
identifying 2-D mask images with confidence levels that satisfy a predetermined confidence threshold, wherein the structure is segmented from the 3-D image only with the identified 2-D mask images.

20. The computer-readable storage medium of claim 19, the method further:
   displaying a re-sliced 2-D image with a corresponding 2-D mask overlaid thereover.

* * * * *